United States Patent [19]

McKamey et al.

[11] Patent Number: 5,507,535
[45] Date of Patent: Apr. 16, 1996

[54] CONDUIT SWIVEL CONNECTOR

[76] Inventors: Floyd McKamey, 104 E. Hunter Cir., Oak Ridge, Tenn. 37830; Robert J. Byers, 107 Iroquois Way, Clinton, Tenn. 37716

[21] Appl. No.: 370,186

[22] Filed: Jan. 9, 1995

[51] Int. Cl.⁶ ............................. A61M 25/00; F16L 27/08
[52] U.S. Cl. ..................... 285/168; 285/276; 285/272; 285/370; 128/912; 604/283
[58] Field of Search ....................... 285/168, 163, 285/226, 281, 272, 370; 604/283, 905; 128/912

[56] References Cited

U.S. PATENT DOCUMENTS

| | | | |
|---|---|---|---|
| 3,076,667 | 2/1963 | Kunger | 285/168 |
| 3,216,746 | 11/1965 | Watts | 285/370 |
| 3,900,221 | 8/1975 | Fouts | 285/168 |
| 4,214,586 | 7/1980 | Merille | 285/370 |
| 4,593,415 | 6/1986 | Vykukal | 285/168 |
| 4,594,734 | 6/1986 | Vykukal | 281/168 |
| 4,597,594 | 7/1986 | Kacalieef et al. | 285/397 |
| 4,676,241 | 6/1987 | Webb et al. | 285/168 |
| 5,405,339 | 4/1995 | Konnen et al. | 604/283 |

*Primary Examiner*—Eric K. Nicholson

[57] ABSTRACT

A conduit swivel connector comprising a unitary central member having a medially oriented abutment flange projecting exteriorly of the central member, and a first sleeve rotatably mounted about the central member about a first tube portion, and a second sleeve rotatably mounted about the central member and about a second tube portion, with the tube portions rotatably secured to the sleeve portions employing respective rings received within cooperating grooves of the tube and sleeve portions permitting a hose to be received upon the first sleeve portion permitting the hose to be rotatably connected by the central member.

4 Claims, 4 Drawing Sheets

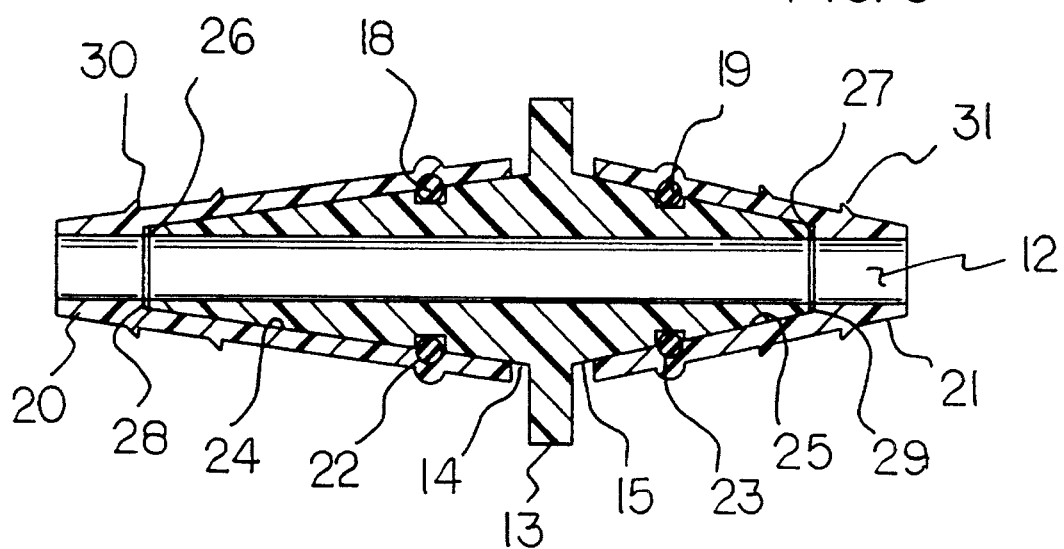
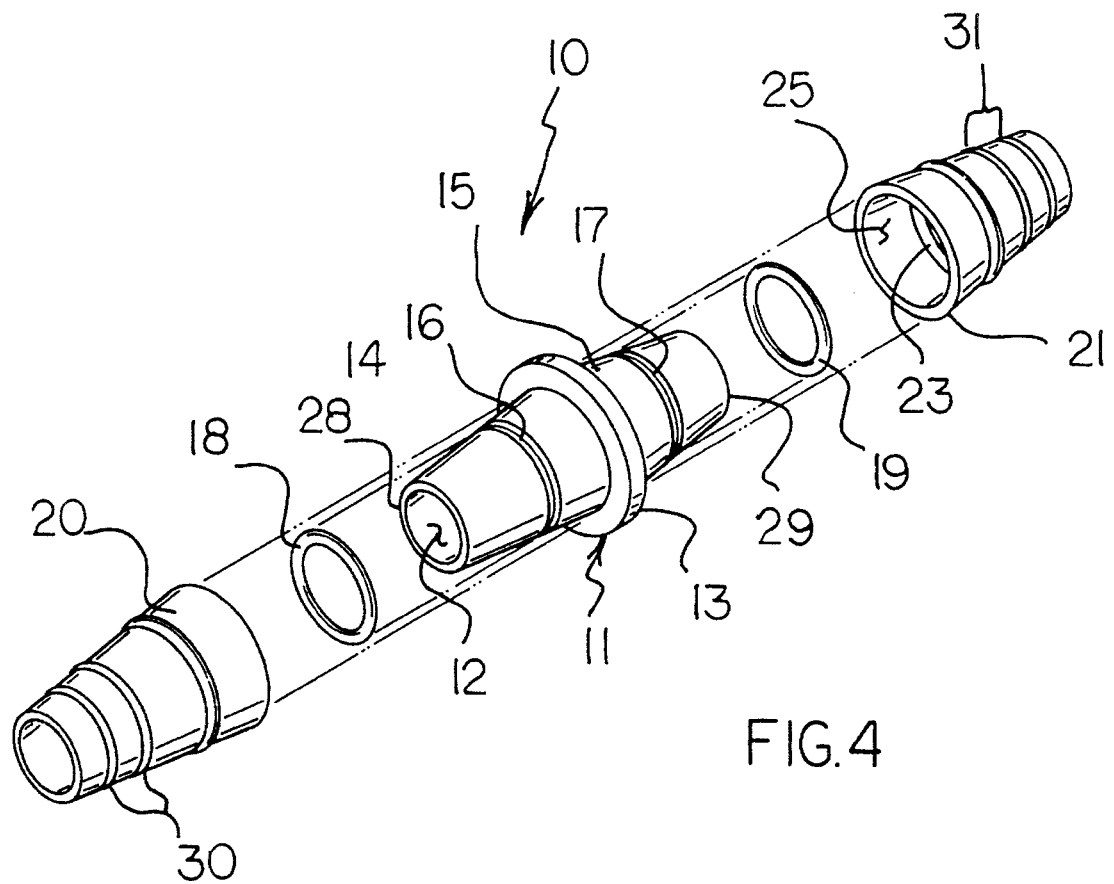

CONDUIT SWIVEL CONNECTOR

TECHNICAL FIELD

The field of invention relates to swivel connector structure for conduits, and more particularly to pneumatic conduits such as in oxygen delivery systems and the like that typically employ flexible tubing to be interconnected. The swivel connection permits the ease of manipulation and utilization of the conduit structure relative to medical patients and the like.

BACKGROUND OF THE INVENTION

Prior art U.S. patents relative to swivel conduit connectors are exemplified by the U.S. Pat. Nos. 3,558,163; 4,909,773; 5,275,444; 4,685,456; 4,946,204; and 5,209,262.

The invention herewithin is directed to improvements over the prior art to provide for a swivel connector structure arranged for ease of use as well as efficiency in construction and economy of manufacture and to this end, it is believed the invention substantially fulfills this need.

SUMMARY OF THE INVENTION

The swivel connector structure of the invention is arranged to include a central member having respective first and second conical tubular portions extending from a central abutment plate, wherein first and second sleeve members are rotatably mounted about the first and second tube portions employing compressible O-ring structure to maintain the tube members in a rotative and coaxially fixed orientation relative to one another.

Objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is a cross-sectional side view of the invention.

FIG. 4 is a perspective exploded illustration of the invention indicating the various components thereof.

DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
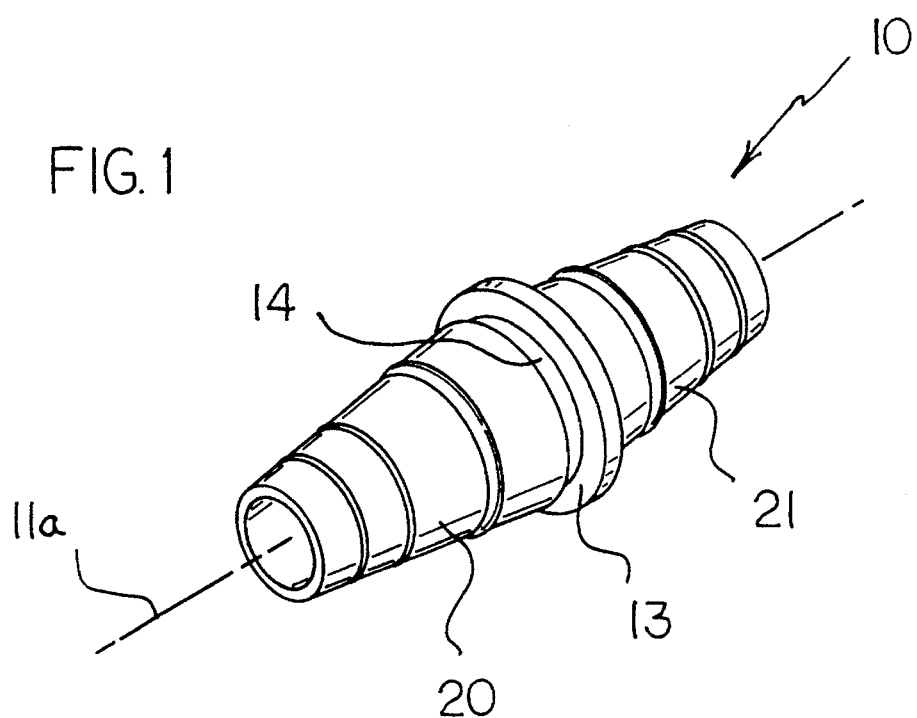
FIG. 1 is a perspective illustration of the invention.
Figure 2:
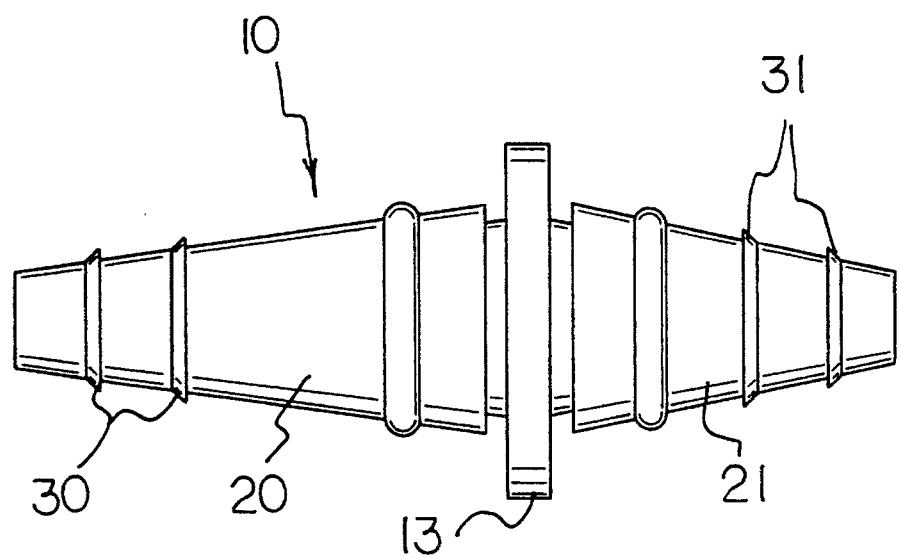
FIG. 2 is a side view, taken in elevation, of the invention.
Figure 5:
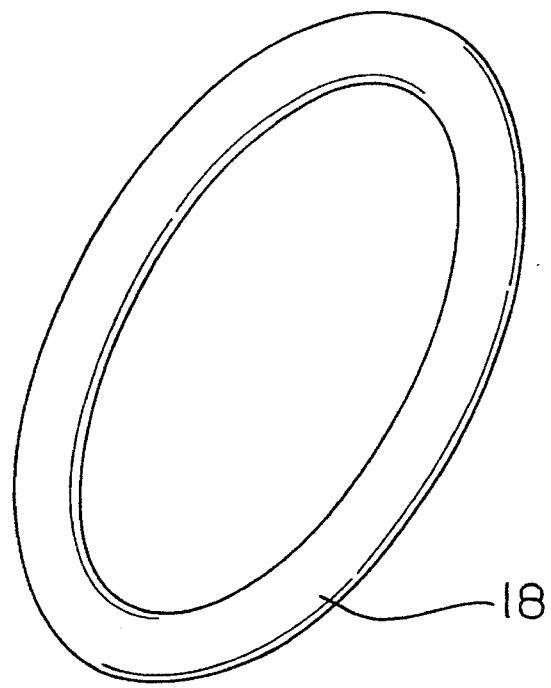
FIG. 5 is a perspective view of a ring member employed by the invention.
Figure 6:
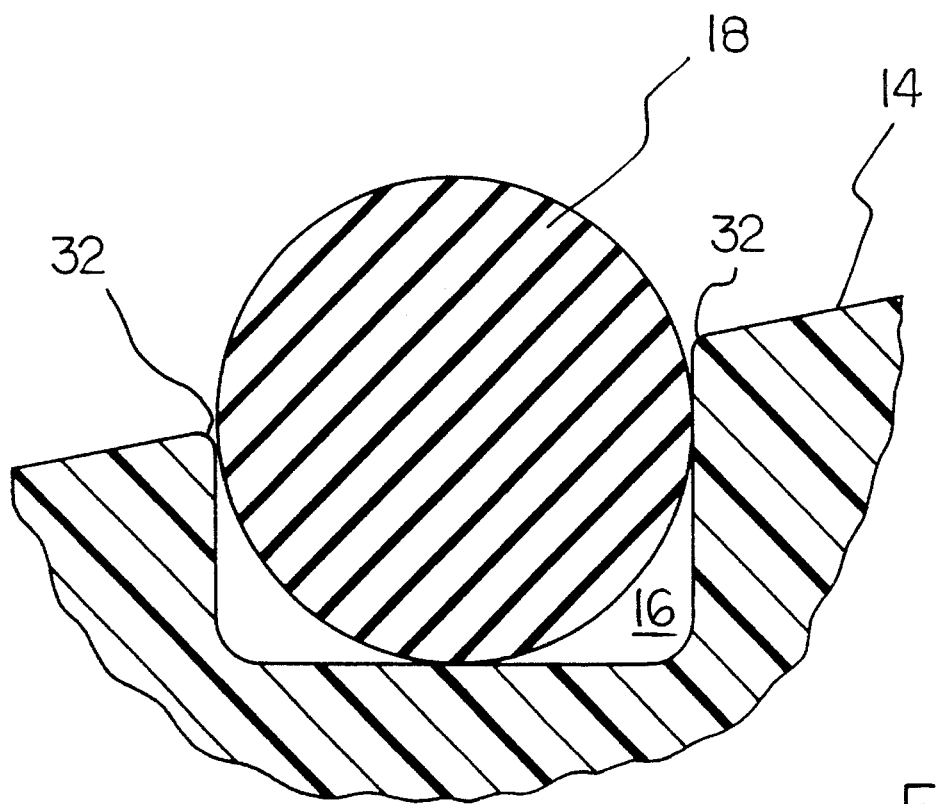
FIG. 6 is a cross-sectional enlarged view of a ring member mounted within a respective groove of the central member.
Figure 7:
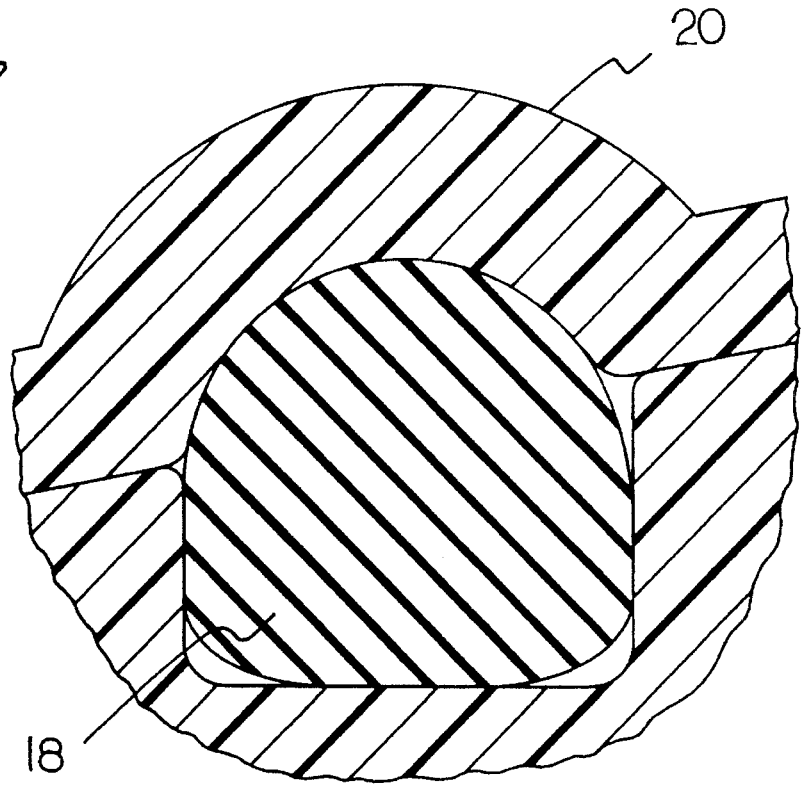
FIG. 7 is an enlarged cross-sectional illustration of the ring member indicated in a compressed configuration relative to the outer tubular portion mounted onto the central member.

The conduit swivel connector 10 of the invention comprises a unitary central member 11 having a through-extending primary conduit 12 directed therethrough, and as indicated substantially coaxially aligned relative to the central member 11. A central abutment flange 13 is fixedly and unitarily mounted onto the central member 11 projecting exteriorly thereof, with the abutment flange 13 indicated as in a substantially orthogonal relationship relative to an axis 11a defined by the central member 11. The central member 11 has extending from the abutment flange 13 respective first and second truncated conical tube portions 14 and 15 that are coaxially aligned relative to the axis 11a, with the first tube portion 14 having a first annular groove 16 and the second tube portion 15 having a second annular groove 17, with the first and second annular grooves 16 and 17 coaxially aligned relative to the axis 11a and directed into an exterior surface of the respective first and second tube portions 14 and 15. Resilient first and second connector rings 18 and 19 are positioned within the respective first and second annular grooves 16 and 17, in a manner as exemplified by the FIG. 6. The respective grooves 16 and 17 include groove arcuate entrance edges 32 (see FIG. 6) to minimize damage to a respective ring of the first and second connector rings 18 and 19 positioned within a respective groove. Such damage may occur in the rotative relationship of respective first and second rotary sleeves 20 and 21 mounted rotatably onto the respective first and second tube portions 14 and 15. The first and second rotary sleeves 20 and 21 are provided with respective first and second sleeve grooves 22 and 23 directed into interior surfaces, or more specifically into the respective first and second sleeve cavities 24 and 25 of the respective first and second rotary sleeves 20 and 21. The respective first and second sleeve grooves 22 and 23 accommodate the respective first and second connector rings 18 and 19 that are positioned within the respective first and second annular grooves 16 and 17 of the respective first and second tube portions 14 and 15. As indicated in the FIG. 7 for example, the rings 18 and 19 are indicated as compressed when the first and second sleeves 20 and 21 are positioned onto the tube portions 14 and 15 respectively. Alternatively, rigid rings may be employed that are merely received within the groove portions of the tube portions 14 and 15 and of the sleeve portions 20 and 21 to maintain the rotary relationship. The compressible aspect of the rings 18 and 19 are provided merely to provide for frictional interaction of the first and second tube portions relative to the first and second sleeve portions to thereby minimize the rotative nature of the sleeves relative to the tube portions.

The respective first and second rotary sleeves 20 and 21 are provided with respective first and second sleeve abutment lips 26 and 27 that are orthogonally oriented relative to the axis 11a and are arranged to abut and engage the central member first and second ends 28 and 29.

Figure 8:
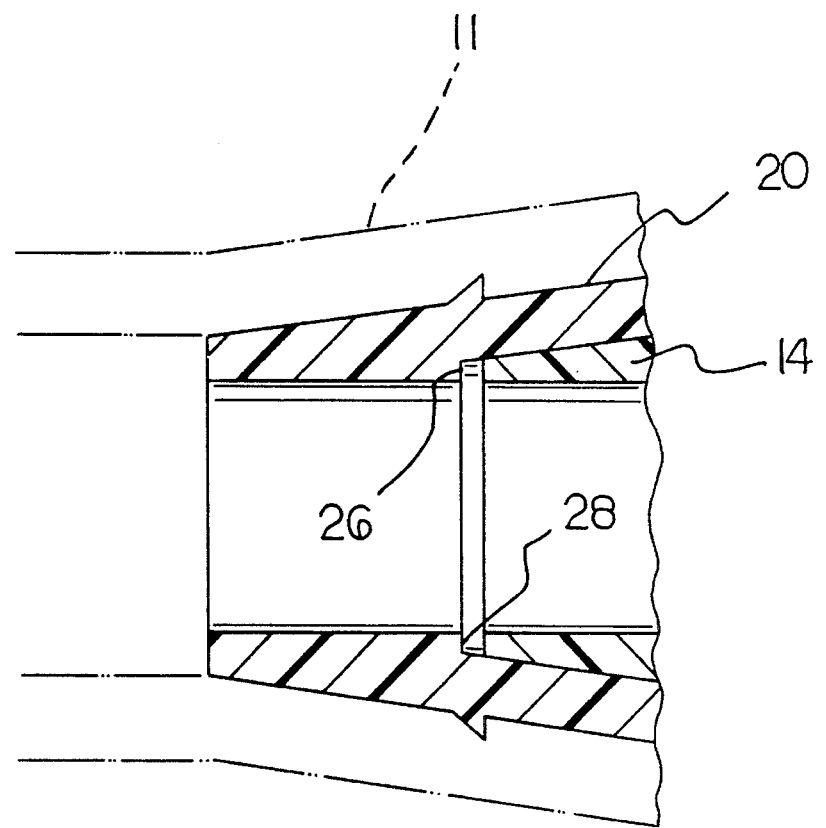
FIG. 8 is an enlarged cross-sectional view indicating a hose portion arranged for mounting onto an outer tubular portion relative to the central member.

To secure a respective flexible hose "H" (see FIG. 8) onto the first and second sleeves 20 and 21, a plurality of respective first and second annular ribs 30 and 31 are mounted to an exterior surface of the respective first and second sleeves 20 and 21 and are canted towards the flange 13 to enhance securement of the hose "H" onto the sleeves in use.

As noted above, the use of rigid first and second rings 18 and 19 may be provided and dimensioned to be freely received within the respective first and second annular grooves 16 and 17, as well as the first and second sleeve grooves 22 and 23 to permit a relatively free rotative relationship of the sleeves 20 and 21 relative to the tube portions 14 and 15.

It is to be understood that while certain forms of the present invention have been illustrated and described herein, it is not to be limited to the specific forms or arrangement of parts described and shown.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed and desired to be protected by Letters Patent of the United States is as follows:

1. A conduit swivel connector, comprising a central member, the central member having a through-extending conduit, and further having an abutment flange fixedly secured to the central member and projecting exteriorly thereof, the central member having respective first and second truncated conical tube portions extending on opposed sides of the abutment flange with the first tube portion having a first sleeve rotatably mounted about said first tube portion and a second sleeve rotatably mounted about said second tube portion, said first sleeve and said second sleeve being coaxially aligned relative to one another wherein said first sleeve includes a first cavity, said second sleeve includes a second cavity, the first and second tube portions each being of a truncated conical configuration, and wherein said first tube portion is complementarily received within the first cavity and said second tube portion is complementarily received within the second cavity, and further, wherein the first tube portion includes a first annular groove and the second tube portion includes a second annular groove, the first annular groove and the second annular groove being coaxially aligned relative to the axis, a first ring received within the first annular groove and a second ring received within the second annular groove, said first sleeve including a first sleeve groove directed into the first sleeve from the first cavity, and a second sleeve groove directed into said second sleeve from the second cavity, and the first ring being received within the first annular groove and the first sleeve groove, and the second ring being received within the second annular groove and the second sleeve groove.

2. A connector as set forth in claim 1 wherein at least the first annular groove includes arcuate entrance edges coextensive with the first annular groove to minimize damage to the first ring.

3. A connector as set forth in claim 2 with the central member having a first end and a second end on opposed sides of the abutment flange, and the central member is unitary and coaxially aligned about the axis, and the first sleeve having a first abutment lip and the second sleeve having a second abutment lip, the first abutment lip within the first cavity, the second abutment lip within the second cavity, and the first abutment lip arranged to engage in a facing relationship relative to the first end, and the second abutment lip arranged in a facing relationship relative to the second end.

4. A connector as set forth in claim 3 wherein the first ring and the second ring are each resilient, and the first ring is compressed within the first sleeve groove, the second ring is compressed within the second sleeve groove.

\* \* \* \* \*